(12) United States Patent
Caspi et al.

(10) Patent No.: US 7,479,380 B2
(45) Date of Patent: Jan. 20, 2009

(54) METHOD FOR ASSESSING BEHAVIORAL PREDISPOSITION

(75) Inventors: Avshalom Caspi, London (GB); Terrie E. Moffitt, London (GB)

(73) Assignee: Wisconsin Alumni Research Foundation, Madison, WI (US)

( * ) Notice: Subject to any disclaimer, the term of this patent is extended or adjusted under 35 U.S.C. 154(b) by 263 days.

(21) Appl. No.: 10/617,453

(22) Filed: Jul. 11, 2003

(65) Prior Publication Data

US 2005/0009035 A1   Jan. 13, 2005

(51) Int. Cl.
*C12P 19/34* (2006.01)
*C12Q 1/68* (2006.01)

(52) U.S. Cl. .......................... 435/91.2; 435/6
(58) Field of Classification Search ........................ None
See application file for complete search history.

(56) References Cited

OTHER PUBLICATIONS

Caspi et al. (Science vol. 297, Aug. 2, 2002, pp. 851-854, and including supplemental material pp. 1-7).*
Wei et al. Eur Psychiatry 1998, vol. 13, pp. 407-410.*
Hamilton et al. (Molecular Psychiatry, 2000, vol. 5, pp. 465-466).*
Norton et al. American Journal of Medical Genetics (Neuropsychiatric Genetics) 2002, 114:491-496.*
Ono et al. American Journal of Medical Genetics (Neuropsychiatric Genetics) 2002, 114:340-342.*
Parsian et al. American Journal of Medical Genetics (Neuropsychiatric Genetics) 1997, 74:475-479.*
Kungi et al. Molecular Psychiatry, 1999, vol. 4, 393-395.*
Caspi A, et al., "Influence of life stress on depression: moderation by a polymorphism in the 5-HTT gene," Science 301:386-389 (2003).
Caspi A, et al., "Moderation of the effect of adolescent-onset cannabis use on adult psychosis by a functional polymorphism in the catechol-O-methyltransferase gene: longitudinal evidence of a gene X environment interaction," Biol. Psychiatry. 57:1117-1127 (2005).
Kim-Cohen J, et al., "MAOA, maltreatment, and gene-environment interaction predicting children's mental health: new evidence and a meta-analysis," Mol. Psychiatry. 11:903-913 (2006).
Moffitt T, et al., "Measured Gene-Environment Interactions in Psychopathology: Concepts, Research Strategies, and Implications for Research, Intervention, and Public Understanding of Genetics," Persp. Psychol. Sci. 1:5-27 (2006).

* cited by examiner

*Primary Examiner*—Juliet C Switzer
(74) *Attorney, Agent, or Firm*—Quarles & Brady LLP (57) ABSTRACT

The present invention relates to diagnostic methods for assessing predisposition of a subject to a mental disorder phenotype having an association with an at-risk allele of a brain-functional gene having a plurality of alleles, the association being conditioned by a pathogenic environmental risk factor status condition. Additionally, the invention relates to methods for discovering a conditional association between a mental disorder phenotype and an at-risk allele of a brain-functional gene having a plurality of alleles, the association being conditioned by a pathogenic environmental risk factor status condition.

5 Claims, 2 Drawing Sheets

METHOD FOR ASSESSING BEHAVIORAL PREDISPOSITION

STATEMENT REGARDING FEDERALLY SPONSORED RESEARCH OR DEVELOPMENT

The present invention was made with US Government funding provided by National Institutes of Health, National Institute of Mental Health, Grant Nos. MH 49414 and MH 45070. The United States Government has certain rights in the invention.

CROSS-REFERENCE TO RELATED APPLICATIONS

Not applicable.

BACKGROUND OF THE INVENTION

A decades long search for conclusive evidence of interplay between genotype and environment to yield a behavioral effect has not succeeded. It has long been postulated that such interplay will exist, but these have not been demonstrated prior to the invention described herein. See Rutter, M. and J. Silberg, "Gene-Environment Interplay in Relation to Emotional and Behavioral Disturbance," *Ann. Rev. Psychol.* 53:463-490 (2002). Demonstration of such an effect would be of great interest to psychiatrists, psychologists, social workers, law enforcement and justice administration personnel, and others involved with behavioral issues.

The invention described in this application relates, in part, to an interaction between a pathogenic environmental risk factor (childhood maltreatment) and a genotype (allelic profile at a genetic locus that encodes monoamine oxidase A, [MAOA]). Childhood maltreatment is a universal risk factor for antisocial behavior. Boys who experience abuse—and more generally, those exposed to erratic, coercive, and punitive parenting—are at risk of developing conduct disorder, evidencing antisocial personality symptoms, and of becoming violent offenders. The earlier children experience maltreatment, the more likely they are to develop these problems. But there are large differences among children in their response to maltreatment. Although maltreatment increases the risk of later criminality by about 50%, most maltreated children do not become delinquents or adult criminals. The reason for this variability in response is largely unknown, but it may be that vulnerability to adversities is conditional upon genetic susceptibility factors.

The MAOA gene, located on the X chromosome (Xp11.23-11.4), encodes the MAOA enzyme, which metabolizes, and renders inactive, neurotransmitters such as norepinephrine (NE), serotonin (5-HT) and dopamine (DA). Genetic deficiencies in MAOA activity have been linked with aggression in mouse and man. Increased aggression, and increased levels of brain NE, 5-HT, and DA, were observed in a transgenic mouse line in which the gene encoding MAOA was deleted, and aggression was normalized by restoring MAOA expression. In humans, a null allele at the MAOA locus was linked with male antisocial behavior in a Dutch kindred. Because MAOA is an X-linked gene, affected males with a single copy produced no MAOA enzyme—effectively, a human knockout. However, this mutation is extremely rare. Evidence for an association between MAOA and aggressive behavior in the human general population remains inconclusive.

Animal studies document that maltreatment stress (e.g., maternal deprivation, peer rearing) in early life alters NE, 5-HT, and DA neurotransmitter systems in ways that can persist into adulthood and influence aggressive behaviors. In humans, altered NE and 5-HT activity are linked to aggressive behavior. Maltreatment has lasting neurochemical correlates in human children. Deficient MAOA activity may dispose the organism toward neural hyper-reactivity to threat, as evidenced by the inhibitory action of phenelzine injections which inhibit the action of monoamine oxidase and prevented rats from habituating to chronic stress. Low MAOA activity may be particularly problematic early in life, because there is insufficient MAOB (a homolog of MAOA with broad specificity to neurotransmitter amines) to compensate for an MAOA deficiency.

BRIEF SUMMARY OF THE INVENTION

The present invention relates, in part, to diagnostic methods for assessing whether a human or a non-human subject is predisposed to a mental disorder phenotype associated with an allele of a brain-functional gene, where a pathogenic environmental risk factor moderates the association between the allele and the phenotype. It is important in the methods to ascertain whether a subject assessed for predisposition to the disorder phenotype has either or both of the contributing genetic and environmental risk factors, or is vulnerable to the environmental risk factor. Similarly, it is important to ascertain the likelihood that a disorder phenotype seen in a subject arises as a result of genetic or environmental influences or both.

Results obtained from such a diagnostic method are advantageously employed in developing appropriate interventions for the subject, prior to or subsequent to the subject experiencing the pathogenic environmental risk factor, or both. In either case, the appropriate pre-emptive or therapeutic intervention can be adjusted in keeping with the findings of the diagnostic methods. At least two related scenarios are envisioned. Pre-emptive interventions designed to prevent or minimize exposure to the environmental pathogen can include counseling a subject to avoid the pathogen, or, if that is not possible, providing the subject with a pre-emptive treatment strategy when the pathogen is apparent. Therapeutic interventions after exposure to the pathogen can include pharmacological therapy and counseling therapy. One can also select one or more populations of individuals for participation in a pharmaceutical screening protocol on the basis of a combination of genotype and experience with the pathogenic environmental risk factor by the individuals.

In another aspect, the present invention is summarized in that in a first diagnostic method for assessing predisposition of a subject to a disorder phenotype having an association with an at-risk allele of a brain-functional gene, the association being conditioned by a pathogenic environmental risk factor status condition, where the subject that has experienced, or is at risk of experiencing, the environmental risk factor, the method includes the steps of determining whether the subject carries one or more copies of an at-risk allele, and concluding that the subject is predisposed to the phenotype if the subject carries the at-risk allele.

In a related aspect, the present invention is summarized in that in a second diagnostic method for assessing predisposition of a subject to a disorder phenotype having an association with an at-risk allele of a brain-functional gene, the association being conditioned by a pathogenic environmental risk factor status condition, where the subject carries the at-risk allele, the method includes the steps of determining whether the subject has experienced or is at risk of experiencing the environmental risk factor, and concluding that the subject is predisposed to the phenotype if the subject has experienced or is at risk of experiencing the environmental risk factor.

In yet another related aspect, the present invention is summarized in that in a third diagnostic method for assessing predisposition of a subject to a disorder phenotype having an association with an at-risk allele of a brain-functional gene, the association being conditioned by a pathogenic environmental risk factor status condition, the method includes the steps of determining whether the subject carries the at-risk allele and determining whether the subject has experienced or is at risk of experiencing the environmental risk factor, the subject being predisposed to the phenotype if the subject carries the at-risk allele and has experienced or is at risk of experiencing the environmental risk factor.

The invention also relates to methods for discovering, in the first instance, a conditional association between an allele of a brain-functional gene and a mental disorder phenotype, where the association is conditioned upon a pathogenic environmental risk factor status, such a conditional association being suitable for evaluation in the diagnostic and preventative methods of the invention. One can employ the identified at-risk allele of a brain-functional gene and pathogenic environmental risk factor in any of the disclosed diagnostic methods for assessing whether an individual is predisposed to the associated disorder phenotype.

In a related aspect, such a discovery method includes the steps of identifying at least one a mental disorder phenotype having high or very high heritability coefficient, identifying a pathogenic environmental risk factor that operates on the at least one phenotype via non-genetic means and having at least higher and lower risk status conditions; ascertaining in a population of individuals an allelic profile for at least one brain-functional gene having an at-risk allele and at least one other allele, and selecting from the at least one disorder phenotype a disorder phenotype that correlates with statistical significance in the population with the at-risk allele only under the higher risk status condition, but which lacks statistically significant correlation with the at-risk allele under the lower risk status condition.

Methods for identifying a conditional association between an allele and a disorder phenotype, where the association is conditioned by a pathogenic environmental risk factor status condition, employ the well-characterized method of moderated multiple regression analysis to test for statistical interaction effects. See, Aiken, L. S. and S. G. West, *Multiple regression: Testing and Interpreting Interactions*, Thousand Oaks, Calif.: Sage (1991) and Long, S. J., *Regression Models for Categorical and Limited Dependent Variables*, Thousand Oaks, Calif.: Sage (1997), both incorporated by reference as if set forth herein in its entirety. Accordingly, it will be apparent that the present invention disclosure puts into the hands of the skilled artisan the ability to construct a matrix in which any or all of a plurality of pathogenic environmental risk factors, disorder phenotypes, and known alleles of brain-functional genes can be evaluated as described herein, preferably using a computing device for routine computations, to identify other conditional interactions between alleles and disorder phenotypes, where the interactions are conditioned by a pathogenic environmental risk factor status condition. Although such an analysis is necessarily complex, no undue experimentation is required, as all necessary information is either readily available to the skilled artisan or can be acquired by careful data acquisition and analysis as the inventors here describe.

In an important aspect of the invention, a mental disorder phenotype suitable for evaluation in a diagnostic method of the invention is a behavioral disorder phenotype (e.g., antisocial behavior or psychosis), an emotional disorder phenotype (e.g., depression or anxiety), or a cognitive disorder phenotype (e.g., dementia or reading disability), as those terms are defined in the Diagnostic and Statistical Manual of Mental Disorders ("DSM"), in which genetic variation in a population accounts for a high or very high proportion of total phenotypic population variation. This "heritability coefficient" (h-squared), a known measure of the likelihood that interactions between at least one gene and at least one environmental risk factor are affecting the phenotype, can be calculated by evaluating how much more similar the behavioral phenotype is for monozygotic (MZ) twin pairs than for dizygotic (DZ) twin pairs, using, e.g., newly collected data or data from prior published studies. A disorder phenotype is suited for further consideration in the methods of the invention when the heritability coefficient is greater than about 30% (high), and is preferably greater than 50% (very high). At a heritability coefficient of, e.g., 30%, 30% of variation in the human population can be explained by genes and their interactions with environmental pathogens, while the other 50% is explained by direct environmental effects that are not conditional on genes. The fourth edition of the DSM (DSM-IV), the current version as of the application date, is incorporated by reference as if set forth herein in its entirety. It will be appreciated, however, that DSM is updated periodically and that the principles of the invention will apply with equal force to mental disorder phenotypes described and cataloged in subsequent editions, as well.

An exemplary mental disorder phenotype of interest in the methods of the invention is antisocial behavior disorder, vis juvenile conduct disorder (CD, manifested by children) and antisocial personality disorder (ASPD, manifested by adults), as specified in the DSM. Measures of antisocial outcomes can include: (1) psychiatric diagnosis of juvenile conduct disorder as specified in the DSM (persistent fighting, bullying, lying, stealing, cruelty to people or animals, vandalism, and disobeying rules), (2) official court records of conviction for violent offenses (assault, robbery, rape, domestic violence, homicide), (3) aggressive personality traits (willingness to harm others for own advantage, interest in and enjoyment of violent material), and (4) symptoms of adult antisocial personality disorder as specified in the DSM (a long-term history of repeated law violations, deceitfulness, conning, impulsivity, physical aggression, and irresponsibility with respect to jobs, spouse, or children, plus lack of remorse).

In a related important aspect of the invention, a pathogenic environmental risk factor is a non-genetic risk factor that is shown to increase risk of psychiatric disorder, and which is conditional on genotype. For example, in an exemplified embodiment, the environmental risk factor is a psychological trauma or psychosocial stress that operates on the disorder phenotype via non-genetic means. In accord with this embodiment, the pathogenic environmental risk factor is considered to be present in a subject if the subject has experienced the psychological trauma or psychosocial stress to an extent considered to be clinically significant in accord with the guidelines set forth in the DSM (e.g., in DSM-IV at pages 29-30 "Axis IV: Psychosocial and environmental problems"). In other embodiments, the environmental risk factor need not be psychological, but can include, without limitation, such varied risk factors as a subject's unhealthy diet, exposure to an infectious or toxic agent, experience with a pharmacological agent (including a natural or a synthetic drug), medical trauma or injury, and the like.

It is duly noted that a pathogenic environmental risk factor can be a predictive risk factor for a plurality of disorders, some having a genetic component and others having no such component. Nevertheless, an important aspect of a pathogenic environmental risk factor suitable for consideration in the methods of the invention is that the risk factor be predictive of the disorder phenotype of interest for, at least in part, non-genetic reasons. Although one can identify candidate risk factors by combing the existing literature for environmental risk factors purported to statistically predict a disorder phenotype, the methods of the invention presuppose an exclusion of those risk factors in which an apparent environmental risk factor masks a genetic risk factor operating on the disorder phenotype. It is noted that a pathogenic environmental risk factor is allowed to predict psychiatric outcome for genetic reasons in part if it also has proven environmental reasons. Some risk factors will involve both genetic and environmental reasons. However, a risk factor cannot be environmental if it predicts an outcome for only genetic reasons.

Moreover, one need not rely upon previously identified pathogenic environmental risk factors for use in the methods of the invention, but can instead identify novel pathogenic environmental risk factors, as long as risk factors having a hidden genetic risk component that operates on the disorder phenotype are excluded from use in the method by employing suitable research designs. Various research designs are described in Rutter, M. et al., "Testing Hypotheses on Specific Environmental Causal Effects on Behavior," *Psychological Bulletin* 127:291-324 (2001), incorporated by reference as if set forth herein in its entirety.

In still another important and a related aspect, a suitable allele of a gene that interacts with a pathogenic environmental risk factor operating upon a disorder phenotype having a high or very high heritability coefficient is an allele of a gene having brain functionality, as the term is understood in the art. Several non-limiting examples of genes having brain functionality are genes expressed in a cell type known to act in the brain, genes associated with variation in size of a brain structure, genes associated with concentration of a neurotransmitter in the brain, genes associated with brain responses to stimuli as assessed by an imaging method such as magnetic resonance imaging, and genes which when altered affect behavior of a human or non-human animal, such as a mammal or a rodent. The skilled artisan will appreciate that brain-functionality can be documented by various research methods such as biochemical analysis of brain tissue or cells obtained from human and non-human animals, as well as research on living non-human animals.

A plurality of alleles having distinct brain-functionality (e.g., high and low levels of expression in the brain) can arise from one or more polymorphisms in a region of a gene that encodes a polypeptide or can be in a regulatory control sequence that affects expression of the polypeptide, such as a promoter or polyadenylation sequence. Alternatively, relevant alleles can arise from one or more polymorphism at a locus distal to a gene having a direct effect in the identified behavior, wherein the product of that distal locus has an indirect effect on the behavior. A relevant allele can affect a polypeptide at a transcriptional or a translational level and can affect a polypeptide's transcription rate, translation rate, degradation rate, or activity. Differences between alleles at a brain-functional gene can be characterized in a sample from a subject or from a plurality of subjects by methods for assaying any of the foregoing that are well-known to the skilled artisan. Such methods can include, but are not limited to measuring an amount of an encoded polypeptide and measuring the potential for a polynucleotide sequence to be expressed. Assay methods can detect proteins or nucleic acids directly or indirectly. One can evaluate the suitability of an upstream promoter region for directing transcription of a coding region of the polynucleotide that encodes a polypeptide or can evaluate the suitability of the coding region for encoding a functional polypeptide. The assay methods are specifically contemplated to include screening for the presence of particular sequences or structures of nucleic acids or polypeptides using, e.g., any of various known microarray technologies.

It will be fully appreciated by the skilled artisan that the allele need not have previously been shown to have had any link or association with the disorder phenotype. Instead, an allele and a pathogenic environmental risk factor can interact to predict a predisposition to a disorder phenotype even when neither the allele nor the risk factor bears any direct relation to the disorder phenotype. This aspect of the invention is depicted in the accompanying detailed description of a preferred embodiment, where hidden effects of alleles were revealed only when the environmental risk factor variable was included in the analysis.

A brain-functional gene of interest is the gene for the neurotransmitter-metabolizing enzyme monoamine oxidase A (MAOA). The gene is known to have two alleles, characterized by a low level and a high level of MAOA protein in the brain, respectively. Genetic deficiencies in MAOA activity have been linked with aggression in mice and in humans, as was noted in the Background of the Invention. However, no conclusive association exists between a "low activity" MAOA allele and such behavior in the human population generally. Moreover, this genotype does not by itself predict violent or antisocial behavior. About ⅓ of human males carry a low-activity MAOA allele.

In another related aspect, the invention is summarized in that a particular embodiment of a diagnostic method of the invention is recognized when the higher risk pathogenic environmental risk factor status is experience of a childhood psychological trauma, the at-risk allele is a "low activity" allele of the human monoamine oxidase A gene that reduces expression of the monoamine oxidase A protein relative to normal level, and the conditional disorder phenotype is antisocial behavior disorder. A subject is predisposed to the disorder when the subject carries the "low activity" allele and has experienced or is at risk of experiencing the trauma. A "low activity" allele of MAOA gene is well known and has been characterized. See Detailed Description for characterization.

It will also be appreciated that the invention facilitates identifying in an individual a positive or negative trait or strength that could warrant counseling the subject to pursue or avoid a particular type of employment. For example, an individual having no identified predisposition toward antisocial behavior might be encouraged toward a career in law enforcement.

Similarly, the link appreciated by the inventors facilitates testing of individuals who have yet to experience (or may never experience) the relevant environmental risk factor, such that an individual determined to carry the subject genetic attribute can be counseled or directed to avoid the environmental risk factor. Additionally, the subject can receive therapy of a psychological or pharmaceutical nature. Prior to the invention by the applicants, the skilled person would not have appreciated the need for vigilant monitoring and treatment of such individuals in that regard.

In yet another related embodiment, the invention is summarized in that a kit for use with a preventative or diagnostic method of the invention comprises (1) a questionnaire that solicits input about a subject relevant to the subject's experience with at least one of (a) a pathogenic environmental risk factor and (b) a disorder phenotype, and (2) a system for obtaining from the subject a sample suitable for producing an allelic profile of at least one brain-functional gene. Optionally, a kit of the present invention can further comprise an assay system for producing the allelic profile of at least one brain-functional gene.

In a preferred embodiment, allelic profiling can be accomplished using a nucleic acid microarray, which can also be commercialized alone or in combination with one or more of the aforementioned kit components. The genetic diagnostic testing field is rapidly evolving and, as such, the skilled artisan will appreciate that a wide range of profiling tests exist, and will be developed, to determine the allelic profile of individuals in accord with the invention.

It is an object of the present invention to provide a systematic method for finding a significant predisposition to a behavior characterized by the combination of an identified allele at a genetic locus and an identified environmental stimulus.

It is an advantage of the present invention that the discovery methods of the invention yield quantitative indications of statistical significance in the Gene x Environment interaction term that instructively guide the artisan in development of diagnostic methods of the invention.

It is a feature and an advantage of the invention that an allele and a pathogenic environmental risk factor can interact to predict a predisposition to a disorder even when neither the allele nor the risk factor bears any direct relation to the disorder. Accordingly, even if the prior knowledge in the art does not show a relationship between an allele of a brain-functional gene and a disorder phenotype, one can still use the discovery methods of the invention to ascertain a previously hidden link between the allele and the disorder.

It is a related feature of the invention that the discovery methods determine whether a disorder phenotype correlates with the allele in a high risk environmental condition while not correlating with the allele in a low risk environmental condition. Accordingly, the effect of the allele is conditional upon the environment. In other words, the allele moderates the effect of the environment on the behavior disorder phenotype.

Other objects, advantages and features of the present invention will become apparent upon consideration of the following detailed description.

BRIEF DESCRIPTION OF THE SEVERAL VIEWS OF THE DRAWINGS

FIG. 2 depicts the association between childhood maltreatment and subsequent antisocial behavior as a function of MAOA activity. (A) Percentage of males (and standard errors) meeting diagnostic criteria for Conduct Disorder between ages 10-18. In a hierarchical logistic regression model, the interaction between maltreatment and MAOA activity was in the predicted direction, b=−0.63, SE=0.33, z=1.87, p=0.06. Probing the interaction within each genotype group showed that the effect of maltreatment was highly significant in the low-MAOA activity group (b=0.96, SE=0.27, z=3.55, p<0.001), and marginally significant in the high-MAOA group (b=0.34, SE=0.20, z=1.72, p=0.09). (B) Percentage of males convicted of a violent crime by age 26. The G×E interaction was in the predicted direction, b=−0.83, SE=0.42, z=1.955, p=0.05. Probing the interaction, the effect of maltreatment was significant in the low-MAOA activity group (b=1.20, SE=0.33, z=3.65, p<0.001), but was not significant in the high-MAOA group (b=0.37, SE=0.27, z=1.38, p=0.17). (C) Mean z-scores (M=0, SD=1) on the Disposition Toward Violence scale at age 26. In a hierarchical ordinary least squares (OLS) regression model, the G×E interaction was in the predicted direction (b=−0.24, SE=0.15, t=1.62, p=0.10); the effect of maltreatment was significant in the low-MAOA activity group (b=0.35, SE=0.11, t=3.09, p=0.002) but not in the high-MAOA group (b=0.12, SE=0.07, t=1.34, p=0.17). (D) Mean z-scores (M=0, SD=1) on the Antisocial Personality Disorder symptom scale at age 26. The G×E interaction was in the predicted direction (b=−0.31, SE=0.15, t=2.02, p=0.04); the effect of maltreatment was significant in the low-MAOA activity group (b=0.45, SE=0.12, t=3.83, p<0.001) but not in the high-MAOA group (b=0.14, SE=0.09, t=1.57, p=0.12).

DETAILED DESCRIPTION OF THE INVENTION

We studied a large sample of male children from birth to adulthood to determine why some children who are maltreated grow up to develop antisocial behavior whereas others do not. A functional polymorphism in the gene encoding the neurotransmitter metabolizing enzyme monoamine oxidase A (MAOA) was found to moderate the effect of maltreatment. Maltreated children with a genotype conferring high levels of MAOA expression were less likely to develop antisocial problems. These findings may partly explain why not all victims of maltreatment grow up to victimize others, and they provide epidemiological evidence that genotypes can moderate children's sensitivity to environmental insults. In this study, individual differences at a functional polymorphism in the promoter of the monoamine oxidase A (MAOA) gene were used to characterize genetic susceptibility to maltreatment and to test whether the MAOA gene modifies the influence of maltreatment on children's development of antisocial behavior.

Based on the hypothesis that MAOA genotype can moderate the influence of childhood maltreatment on neural systems implicated in antisocial behavior, we tested whether antisocial behavior would be predicted by an interaction between a gene (MAOA) and an environment (maltreatment). A well-characterized variable number tandem repeat (VNTR) polymorphism exists at the promoter of the MAOA gene, which is known to affect expression. We genotyped this polymorphism in members of the Dunedin Multidisciplinary Health and Development Study, a sample without population stratification confounds. The history of the Study is described in P. A. Silva, W. Stanton, Eds. *From Child to Adult: The Dunedin Study* (Oxford University Press, 1996). This birth cohort of 1,037 children (52% male) has been assessed at ages 3, 5, 7, 9, 11, 13, 15, 18, 21, and was virtually intact (96%, N=499 males) at age 26 years.

Research Sample. The Dunedin longitudinal study was constituted at age 3 when the investigators enrolled 91% of the consecutive births between April 1972 and March 1973 in Dunedin, New Zealand. Cohort families represent the full range of socioeconomic status in the general population of New Zealand's South Island. Follow-ups have been carried out at ages 3, 5, 7, 9, 11, 13, 15, 18, 21, and most recently at age 26, when we assessed 96% of the living cohort members (N=499 males). At each age, participants are brought back to the research unit within 60 days of their birthday for a full day of individual tests and interviews. These data are supplemented by questionnaires completed by persons who know the Study members well and by official record searches.

DNA extraction and genotyping. At age 26, DNA was obtained from 953 Study members (97% of those assessed at that age; 51% male); 93% of DNA samples were obtained via blood and 7% via buccal swabs for those not wishing to undergo phlebotomy. DNA was extracted from blood samples using standard procedures. A modified procedure was used to extract DNA from buccal cells. Primer sequences are described by Sabol et al., namely MAO APT1 (5'-ACAGCCTGACCGTGGAGAAG-3'; SEQ ID NO:1) and MAO APB1 (5'-GAACGGACGCTCCATTCGGA-3'; SEQ ID NO: 2), although here MAO APT1 was 5'-labelled with the TET fluorophore. PCR was carried out on a PTC-225 DNA engine (MJ Research), using the following cycling conditions: initial 2-min denaturing step at 95° C., followed by 35 cycles of 94° C. for 1 min, 58.2° C. for 1 min and 72° C. for 1 min 30 secs, and a final extension phase of 72° C. for 5 min. Reactions were performed in 25 µl GeneAmp PCR Buffer I (PE Applied Biosystems), 1.5 mM $MgCl_2$, 50 ng of genomic DNA, 10 pmols of each primer, 0.33 mM dNTPs and 1.5 units of Native Taq (Promega). PCR products were assayed on an Applied Biosystems 377 Genetic Analyzer (PE Applied Biosystems), set up in genotyping mode, using 4.25% w/v polyacrylamide gel (Amresco) and TAMRA-labelled GS500 (PE Applied Biosystems) size standard. Results were analyzed using GeneScan v2.1 and Genotyper v1.1 software (Applied Biosystems).

Table 1 shows the allele frequencies observed among non-Maori members of our Study. The genotypes were classified according to previous results showing that an optimum sequence length of 3.5 or 4 repeats results in high expression levels. In terms of expression, all studies agree on the functional classification of the two most common alleles, i.e. 3 repeats (low activity) and 4 repeats (high activity). These two alleles account for 95.7% of our sample. Of rare alleles, both Sabol et al. and Deckert et al. assayed the 3.5 repeat with the same result (high activity), whereas a discrepancy arises for the 5 repeat. We chose the classification of Sabol et al. as they assayed 3 cell lines as opposed to one. However, we carried out analyses using both classifications and observed the same effects. The rare 2 repeat, of which only 1 exists in our sample, was classified as low activity due to its short length.

TABLE 1

The Dunedin sample does not differ significantly from published frequencies of alleles (5, 7) at the MAO A promoter locus, $X^2$ (4) = 6.21, p = 0.184.

| | Number of repeats at MAOA promoter polymorphism | | | | |
|---|---|---|---|---|---|
| | 2 | 3 | 3.5 | 4 | 5 |
| Number (and percent) of alleles in Dunedin sample males, n (chromosomes) = 442 | 1 (0.2) | 149 (33.7) | 5 (1.1) | 274 (62.0) | 13 (2.9) |
| Number (and percent) of alleles in Caucasian controls, n (chromosomes) = 1940 | 3 (0.2) | 658 (33.9) | 9 (0.5) | 1238 (63.8) | 32 (1.6) |

Population stratification can probably be ruled out as a confounding factor in this study. First, cohort members reporting Maori ethnicity (7%) were not included in our analysis. Second, Caucasian study members reported the ethnicity of all four grandparents, and only 4% reported 1 or 2 non-European grandparents. Third, allele frequencies among Caucasian study members matched closely frequencies reported in Caucasian samples. As a final check for stratification we adopted a genomic control approach based on latent class analysis. One hundred individuals were selected at random from the sample and typed for 40 unlinked microsatellite markers. In a stratified sample one would expect to observe Hardy-Weinberg disequilibrium and linkage disequilibrium across the unlinked markers: our genomic control approach aimed to identify subpopulations (latent classes) such that within each there is Hardy-Weinberg and linkage equilibrium. In the current sample, however, there was no support for having more than one latent class, which is consistent with the sample being homogeneous.

Childhood maltreatment. Evidence of childhood maltreatment during the first decade of life (ages 3 to 11 years) was ascertained using behavioral observations, parental reports, and retrospective reports by Study members once they reached adulthood. First, mother-child interactions were observed during the child's age-3 assessment. The mother was rated by an observer on eight categories: mother's affect toward the child was consistently negative; harshness toward the child; rough, awkward handling of the child; no effort to help child; unaware or unresponsive to child's needs; indifferent to child's performance; demanding of child's attention; soiled, unkempt appearance of child). Mothers engaging in 2 or more such behaviors were classified as rejecting (16%), based on evidence that such maternal behavior is associated with increased risk of children's later antisocial behavior. Second, harsh discipline was measured at ages 7 and 9 using a checklist on which parents indicated if they engaged in ten disciplinary behaviors such as "smack him or hit him with something." Parents scoring in the top decile of the sample-wide distribution were classified as unusually harsh, relative to the culture in which this cohort grew up (10%), based on evidence that such parenting styles are associated with subsequent antisocial behavior of children. Third, changes in the person occupying the role of the child's primary caregiver were ascertained at each assessment. Children who experienced 2 or more such changes during the first decade of life were classified as having suffered disruptive caregiver changes (6%), based on evidence that such family changes are predictive of later antisocial behavior. Fourth, exposure to child physical abuse was assessed retrospectively at age 26 as part of an interview about victimization. Study members were classified as physically abused if they reported multiple episodes of severe physical punishment (e.g., strapping leaving welts; whipping with electric cords) resulting in lasting bruising or injury before age 11 (3%). Fifth, unwanted sexual contact was assessed retrospectively at age 26 as part of an interview about reproductive health. Study members were classified as sexually abused if they reported having their genitals touched, touching another's genitals, or attempted/completed sexual intercourse before age 11 (5%). The percentages of males experiencing physical and sexual abuse are consistent with rates reported elsewhere. We examined these maltreatment experiences based on evidence that they too are linked to antisocial behavior. We derived a cumulative exposure index for each child by counting the number of maltreatment experiences during the first decade of life; 64% of the children experienced no maltreatment, 28% experienced 1 indicator of maltreatment (hereafter referred to as "probable maltreatment"), and 8% experienced 2 or more indicators of maltreatment (hereafter "severe maltreatment").

Antisocial behavior outcomes in adolescence and in adulthood. We examined four different outcome measures of antisocial behavior, using information from independent data sources that were appropriate at different stages of development.

Conduct disorder was measured according to the criteria of the Diagnostic and Statistical Manual of Mental Disorders (DSM), which identify adolescents displaying a persistent pattern of behavior that violates the rights of others, including physical harm. A diagnosis of conduct disorder (using a 12-month reporting period for symptoms) was made in our longitudinal study when we assessed the research participants at each of four ages: ages 11, 13, 15, and 18. A 'lifetime' diagnosis was arrived at by establishing whether a Study member received the diagnosis at one or more of the four ages (according to the DSM, conduct disorder is not normally diagnosed after age 18).

Court records of violent convictions in adulthood were searched via the Australian and New Zealand Police for 97% of male Study members. Among Study males, 11% received 174 convictions for violent crimes (e.g., common assault, aggravated assault with intent to injure with weapon, domestic violence, manslaughter, rape).

A disposition toward violence was ascertained at age 26 as part of the Multidimensional Personality Questionnaire (MPQ) Aggression scale (e.g., "When I get angry I am ready to hit someone," "I admit that I sometimes enjoy hurting someone physically"). α reliability of the summed scale was 0.71.

Symptoms of antisocial personality disorder were ascertained at age 26, when informant reports about 95% of male Study members were collected by mailing a questionnaire to persons they nominated as "someone who knows you well". Informants were friends, partners, or family members. Informants described the Study members on seven cardinal symptoms: "has problems controlling anger," "blames others for own problems, "does not show guilt after doing something bad," "impulsive, rushes into things without thinking," "good citizen (reversed)," "does things against the law," and "gets into fights." Response options were "not a problem, "a bit of a problem,", and "yes, a problem." α reliability of the summed scale was 0.84.

Intercorrelations between the four outcomes ranged from 0.32 to 0.46. We fitted a common factor model to the four measures of antisocial behavior, using methods appropriate to the mixture of categorical and continuous measures. According to multiple fit indices, the model fit well ($\chi^2$ (2)=2.56, p=0.28, CFI=0.99, RMSEA=0.02), with factor loadings ranging from 0.64 to 0.74, showing that all four measures index liability to antisocial behavior. On the basis of the factor analysis, we created a composite index of antisocial behavior by counting the number of antisocial outcomes observed for each Study member. This summary index counts whether they (a) met diagnostic criteria for adolescent conduct disorder, (b) were convicted for a violent crime, (c) scored in the top quartile of the distribution on a self-reported disposition toward violence, and (d) scored in the top quartile of the distribution on informant-reported antisocial personality disorder symptoms. We created this composite because the most reliable way to measure antisocial behavior is to aggregate multiple sources of information. We also report separate analyses of each of the four measures of antisocial behavior, in order to test whether the observed findings were robust or sensitive to the four different ways in which the antisocial phenotype was measured. A robust finding is one whose pattern should be observed irrespective of how antisocial behavior is measured (20).

The effects of MAOA activity, maltreatment, and their interaction on antisocial behavior were estimated in a moderated regression framework, using logistic regression for categorical outcomes (e.g., conduct disorder) and ordinary least squares (OLS) for continuous measures (e.g., personality disposition toward violence).

The full results are contained in Table 2. The interaction effect was consistent with the hypothesis that MAOA activity moderated the effect of maltreatment on antisocial outcomes. As shown in the Report (FIG. 1), the dose-response association between maltreatment and antisocial behavior was significantly weaker in the high-MAOA activity group than in the low-MAOA activity group. We probed the genexenvironment interaction further (21) and found that the difference in antisocial behavior between the high- and low-MAOA groups became larger at increasing levels of maltreatment. T-tests for these differences are as follows: t=−1.48, p=0.14 at no maltreatment, t=1.62, p=0.11 at probable maltreatment, and t=2.31, p=0.02 at severe maltreatment.

We further considered the possibility that the observed protective effect of high-MAOA activity could have been brought about because of individual differences in IQ. We considered this alternative hypothesis because complete and selective deficiency of enzymatic activity of MAOA was associated with mild mental retardation in the Dutch kindred (22), and low IQ is linked to high levels of antisocial behavior in the general population (23), including in this sample (r=−0.28, p<0.001). Therefore, the observed protective effect of high-MAOA activity could have been an epiphenomenon of higher IQ among males with this genotype. However, we found no IQ differences between males with low- and high-MAOA activity (M=107 (SD=14) vs. M=108 (SD=13), t(430)=−0.70, p=0.48), and no significant linear association between maltreatment and IQ in either the low-MAOA activity group, t(157)=−0.87, p=0.38, or the high-MAOA activity group, t(269)=0.93, p=0.34. We repeated the regression analysis shown in Supplementary Table 2 (first row), with the addition of IQ as a covariate. The interaction effect between MAOA and maltreatment remained statistically significant and of equivalent magnitude after controlling for IQ (b=−0.34, se=0.14, t=2.43, p=0.015).

TABLE 2

Results of final regression analyses testing G × E interaction effects on antisocial outcomes. The Table presents final models with main effects and interactions entered simultaneously.

| Antisocial Outcomes | Predictor Variables | | | | | | | | | | | |
|---|---|---|---|---|---|---|---|---|---|---|---|---|
| | MAOA | | | | Maltreatment[a] | | | | MAOA × Maltreatment | | | |
| | B | se | t/z | p | b | se | t/z | p | b | se | t/z | p |
| Composite Antisocial Index | .16 | .11 | 1.45 | .15 | .54 | .11 | 4.73 | .001 | −.36 | .14 | 2.53 | .01 |
| Conduct Disorder (%) | .06 | .28 | .20 | .84 | .96 | .27 | 3.55 | .001 | −.63 | .33 | 1.87 | .06 |
| Violence Conviction (%) | .32 | .46 | .70 | .48 | 1.2 | .33 | 3.65 | .001 | −.83 | .42 | 1.95 | .05 |

TABLE 2-continued

Results of final regression analyses testing G × E interaction effects on antisocial outcomes. The Table presents final models with main effects and interactions entered simultaneously.

| Antisocial Outcomes | Predictor Variables | | | | | | | | | | | |
|---|---|---|---|---|---|---|---|---|---|---|---|---|
| | MAOA | | | | Maltreatment[a] | | | | MAOA × Maltreatment | | | |
| | B | se | t/z | p | b | se | t/z | p | b | se | t/z | p |
| Disposition Toward Violence Scale | .11 | .11 | .95 | .35 | .35 | .12 | 3.04 | .003 | −.24 | .15 | 1.62 | .10 |
| Antisocial Personality Symptoms Scale | .22 | .12 | 1.90 | .06 | .45 | .12 | 3.74 | .001 | −.31 | .15 | 2.02 | .04 |

[a]Childhood maltreatment was handled as a single quantitative variable in the regression analyses, ranging from no maltreatment to severe maltreatment.

Finally, we considered the possibility that the observed protective effect of high-MAOA activity could be brought about if children with this genotype were likely to be reared in favorable environments. As such, we introduced into our analyses a further environmental covariate, social class, that is associated with antisocial behavior (24), including in this sample (r=−0.46, p<0.001). The childhood social class variable used in our analyses is the average of the highest social class level of either parent, assessed repeatedly at the Study member's birth and ages 3, 5, 7, 9, 11, 13, and 15. This variable reflects the socioeconomic conditions experienced by the Study members while they grew up (25). There were no social class differences between males with low- and high-MAOA activity, t(439)=0.90, p=0.37. We repeated the regression analysis shown in Supplementary Table 2 (first row), with the addition of social class as a covariate. The interaction effect between MAOA and maltreatment remained statistically significant and of equivalent magnitude after controlling for childhood social class origins (b=−0.33, se=0.14, t=2.36, p=0.019).

The Study offers three advantages for testing gene-environment (G×E) interactions. First, in contrast to studies of adjudicated or clinical samples, the representative general population sample avoids potential distortions in association between variables. Second, the sample has well-characterized environmental adversity histories. Between ages 3-11 years, 8% of the Study children experienced "severe" maltreatment, 28% experienced "probable" maltreatment, and 64% experienced no maltreatment. (Maltreatment groups did not differ on MAOA activity, $\chi^2(2)=0.38$, p=0.82, suggesting that genotype did not influence exposure to maltreatment.) Third, the study has ascertained antisocial outcomes rigorously. Antisocial behavior is a complicated phenotype, and each method and data source used to measure it (e.g., clinical diagnoses, personality checklists, official conviction records) is characterized by different strengths and limitations. Using information from independent sources appropriate to different stages of development, we examined four outcome measures. Adolescent conduct disorder was assessed according to criteria of the Diagnostic and Statistical Manual of Mental Disorders (DSM); convictions for violent crimes were identified via the Australian and New Zealand police; a personality disposition toward violence was measured as part of a psychological assessment at age 26; symptoms of antisocial personality disorder were ascertained at age 26 by collecting information about the Study members from people they nominated as "someone who knows you well." A common-factor model fit the four measures of antisocial behavior well, with factor loadings ranging from 0.64 to 0.74, showing that all four measures index liability to antisocial behavior.

Figure 1:
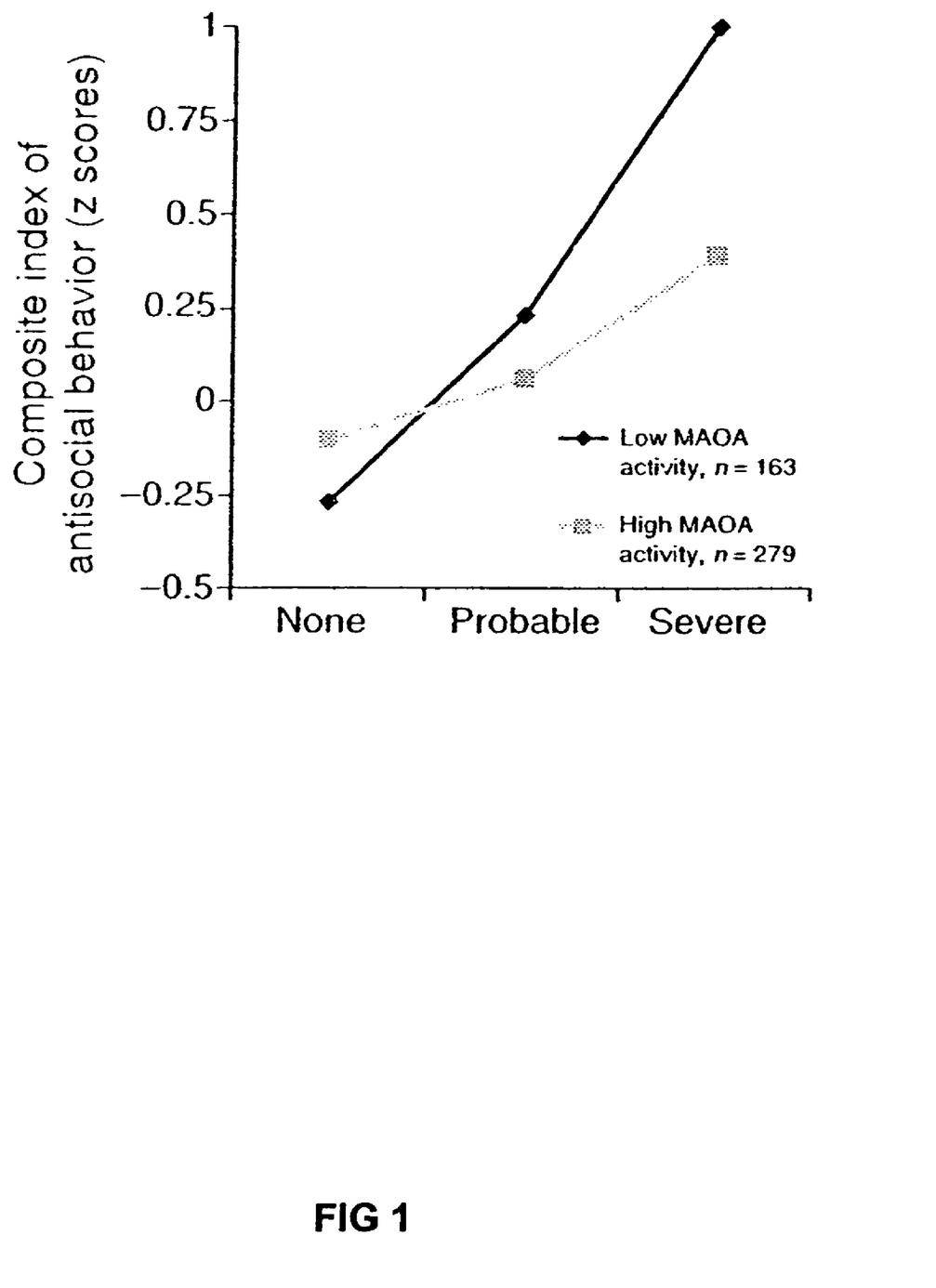
FIG. 1 depicts the means on the composite index of antisocial behavior as a function of MAOA activity and a childhood history of maltreatment. MAOA activity is the gene expression level associated with allelic variants of the functional promoter polymorphism, grouped into low and high activity; childhood maltreatment is grouped into 3 categories of increasing severity. The antisocial behavior composite is standardized (z-score) to a M=0 and SD=1; group differences are interpretable in SD unit differences (d).

Using moderated regression analysis, we predicted scores on a composite antisocial index comprising the four measures of antisocial behavior (FIG. 1). The main effect of MAOA activity on the composite index of antisocial behavior was not significant (b=0.01, SE=0.09, t=0.13, p=0.89) while the main effect of maltreatment was significant (b=0.35, SE=0.07, t=4.82, p<0.001). The hypothesized interaction between MAOA activity and maltreatment revealed a significant G×E interaction (b=−0.36, SE=0.14, t=2.53, p=0.01). Probing the interaction within each genotype group showed that the effect of childhood maltreatment on antisocial behavior was significantly weaker among males with high-MAOA activity (b=0.24, SE=0.11, t=2.15, p=0.03) than among males with low-MAOA activity (b=0.68, SE=0.12, t=5.54, p<0.001).

Figure 2:
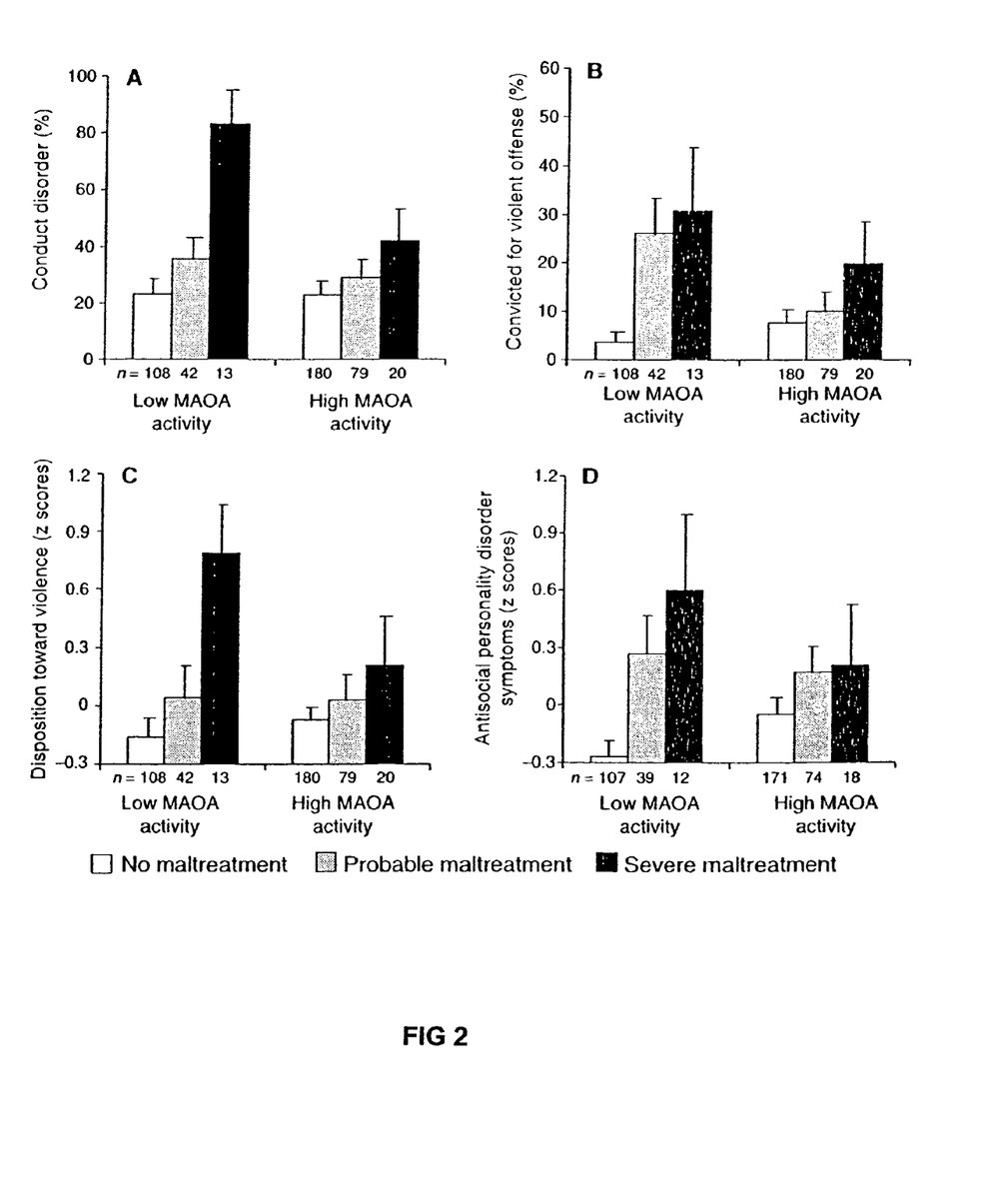

We conducted further analyses to test if the G×E interaction was robust across each of the four measures of antisocial behavior that made up the composite index. For all four antisocial outcomes, the pattern of findings was consistent with the hypothesis that the association between maltreatment and antisocial behavior is conditional, depending on the child's MAOA genotype (G×E interaction p=0.06, 0.05, 0.10, and 0.04, respectively). For adolescent conduct disorder (FIG. 2A), maltreated males (including probable and severe cases) with the low-MAOA activity genotype were more likely than nonmaltreated males to develop conduct disorder by a significant odds ratio of 2.8 (95% CI: 1.42-5.74). In contrast, among males with high-MAOA activity, maltreatment did not confer significant risk for conduct disorder (OR=1.54, 95% CI: 0.89-2.68). For adult violent conviction (FIG. 2B), maltreated males with the low-MAOA activity genotype were more likely than nonmaltreated males to be convicted of a violent crime by a significant odds ratio of 9.8 (95% CI: 3.10-31.15). In contrast, among males with high-MAOA activity, maltreatment did not confer significant risk for violent conviction (OR=1.63, 95% CI=0.72-3.68). For self-reported disposition toward violence (FIG. 2C) and informant-reports of antisocial personality disorder symptoms (FIG. 2D), males with the low-MAOA activity genotype who were maltreated in childhood had significantly elevated antisocial scores relative to their low-MAOA counterparts who were not maltreated. In contrast, males with high-MAOA activity did not have elevated antisocial scores, even when they had experienced childhood maltreatment.

These findings provide initial evidence that a functional polymorphism in the MAOA gene moderates the impact of early childhood maltreatment on the development of antisocial behavior in males. Replications of this GxE interaction are now needed. Replication studies should use valid and reliable ascertainments of maltreatment history and obtain multiple measures of antisocial outcomes, in large samples of males and females. This study focused on males because their single X chromosome yields two straightforwardly characterized MAOA genotypes: high-activity (63% in this sample) and low-activity (37%). Females, having two copies of the X chromosome, fall into two homozygous groups, high-high (42% in this sample), low-low (12%), and a third heterozygous group, low-high (46%), that cannot be characterized with certainty because it is not possible to determine which of the two alleles is inactivated for each female participant. Given the rarity in females of both the low-low genotype (12%) and severe antisocial outcomes, such as violent conviction (2%), our cohort of 481 females, 11% of whom were severely maltreated, was too small to support all of the analyses reported here for males. However, adolescent conduct disorder could be analyzed, revealing that girls with the low-MAOA activity genotype were more likely to develop conduct disorder by a significant odds ratio of 5.5 (95% CI: 1.0-32.0) if they were maltreated. In contrast, among girls with high-MAOA activity, maltreatment did not confer significant risk for conduct disorder (OR=1.7, 95% CI: 0.75-4.2). This suggests that high-MAOA activity exerts a protective influence against maltreatment for girls as well as boys, and raises the possibility that further research into X-linked genotypes may help to explain one of the least understood facts about serious antisocial behavior: the sex difference.

The findings have implications for research and clinical practice. With regard to research in psychiatric genetics, knowledge about environmental context might help gene-hunters refine their phenotypes. Genetic effects in the population may be diluted across all individuals in a given sample, if the effect is apparent only among individuals exposed to specific environmental risks. With regard to research on child health, knowledge about specific genetic risks may help to clarify risk processes. Numerous biological and psychological processes have been put forward to explain why and how experiences of maltreatment are converted into antisocial behavior toward others, but there is no conclusive evidence that any of these processes can account for the progression from childhood maltreatment to later criminal violence. Moreover, some youngsters make the progression, but others do not, and researchers have sought to understand why. The search has focused on social experiences that may protect some children, overlooking a potential protective role of genes. Genes are assumed to create vulnerability to disease, but from an evolutionary perspective they are equally likely to protect against environmental insult. Maltreatment studies may benefit from ascertaining genotypes associated with sensitivity to stress, and the known functional properties of MAOA may point toward hypotheses, based on neurotransmitter system development, about how stressful experiences are converted into antisocial behavior toward others in some, but not all, victims of maltreatment.

Although individuals having the combination of low-activity MAOA genotype and maltreatment were only 12% of the male birth cohort, they were 22% of those with multiple antisocial outcomes, yielding an attributable risk fraction (11%) comparable to that of the major risk factors associated with cardiovascular disease. Moreover, 85% of cohort males having a low-activity MAOA genotype who were severely maltreated developed some form of antisocial behavior. Both attributable risk and predictive sensitivity indicate that these findings could inform the development of future pharmacological treatments.

The present invention is not intended to be limited to the foregoing examples but to encompass all such variations and modifications as fall within the scope of the appended claims.

References, each incorporated by reference as if set forth herein in its entirety Aiken, L. S., S. G. West, *Multiple Regression: Testing and Interpreting Interactions* (Sage, Thousand Oaks, Calif., 1991).
Bennet, A. J., et al., *Molec. Psychiatry* 7, 188 (2002).
Bennan, M. E., R. J. Kavoussi, E. F. Coccaro, in *Handbook of Antisocial Behavior*, D. M. Stoff, Bowtell, D., Anal. Biochem. 162, 463 (1987).
Breiling, J., J. D. Maser, Eds. (Wiley, N.Y., 1997).
Bremner, J. D., E. Vermetten, *Develop. Psychopathol.* 13, 473 (2001).
Brunner, H. G., M. Nele, X. O. Breakefield, H. H. Ropers, B. A. van Oost, *Science* 262, 5133 (1993).
Cases, O., et al., *Science* 268, 1763 (1995).
Cicchetti, D., F. A. Rogosch, *Develop. and Psychopathol.* 13 783 (2001).
Cohen, P., J. Cohen, *Arch. Gen. Psychiatry* 41, 1178 (1984).
De Bellis, M., *Develop. Psychopathol.* 13, 539 (2001).
Deckert, J., et al., *Hum. Mol. Gen.* 8, 621 (1999).
Denney, R. M., H. Koch, I. W. Craig, *Hum. Genet.* 105, 542 (1999). *Diagnostic and Statistical Manual of Mental Disorders*, $4^{th}$ edition (American Psychiatric Association, Washington, D.C., 1994).
Dodge, K. A., J. E., Bates, G. S. Pettit, *Science* 250 1678 (1990)
Fergusson, D. M., L. J. Horwood, M. T. Lynskey, *J. Child Psychol. Psychiatry.* 33, 1059 (1993).
Francis, D. D., M. J. Meany, *Curr. Opin. Neurobiol.* 9 128 (1999).
Freeman, B., et al., *Behav. Genet.* 27, 251 (1997).
Glaser, D., *J. Child Psychol. Psychiatry* 41, 97 (2000).
Grundy, S. M., R. Paternak, P. Greenland, S. Smith, V. Fuster, *J. Am. Coll. Cardiol.* 34 1348 (1999).
Hill, A. V. S., *Br. Med. Bull.* 55, 401 (1999).
Jaffee, S. R., et al. *Arch. Gen. Psychiatry,* 58 215 (2002).
Jeanpierre, M., *Nucleic. Acids. Res.* 15, 9611 (1987).
Johnson, J. G., P. Cohen, J. Brown, E. Smailes, D. P. Bernstein, *Arch. Gen. Psychiatry* 56, 600 (1999).
Jorm, A. F., et al., *Psychiatric Genet.* 10, 87 (2000).
Jorm, A. F., S. Easteal, *Soc. Psychiatry Psychiatr. Epidemiol.* 35, 1 (2000).
Keiley, M. K., T. R. Howe, K. A. Dodge, J. E. Bates, G. S. Pettit, *Develop. Psychopathol.* 13, 891 (2001).

Kendler, K. S., *Arch. Gen. Psychiatry* 58, 1005 (2001).
Kraemer, G. W., M. H. Ebert, D. E. Schmidt, W. T. McKinney, *Neuropsychopharmacology* 2, 175 (1989).
Krueger, R. F., A. Caspi, T. E. Moffitt, *J. Pers.* 68, 967 (2000).
Levy, E. R., J. F. Powell, V. J. Buckle, Y. P. Hsu, X. O. Breakefield, I. W. Craig *Genomics* 5, 368 (1989).
Luthar, S. D., D. Cicchetti, B. Becker, *Child Develop.* 71, 543 (2000).
Lynam, D., T. E. Moffitt, M. Stouthamer-Loeber, *J Ab. Psychol.* 102 187 (1993).
Manuck, S. B., J. D. Flory, R. E. Ferrell, J. J. Mann, M. F. Muldoon, *Psychiatry Res.* 95, 9 (2000).
Moffitt, T. E., A. Caspi, M. Rutter, P. A. Silva, *Sex Differences in Antisocial Behavior: Conduct Disorder, Delinquency, and Violence in the Dunedin Longitudinal Study* (Cambridge University Press, 2001).
Moffitt, T. E., A Caspi, H. Harrington, B. J. Milne, *Develop. Psychopathol.* 14, 179 (2002).
Shih, J. C., K. Chen, M. J. Ridd. *Annu. Rev. Neurosci.* 22, 197 (1999).
Shih, J. C., R. F. Thompson, *Am. J. Hum. Genet.* 65, 593 (1999).
Straus, M. A., D. B. Sugarman, J. Giles-Sims, *Arch. Pediatr. Adolesc. Med.* 151, 761 (1997).
Suomi, S. J., in *Handbook of Developmental Psychopathology*, A. J. Sameroff, M. Lewis, S. Miller, Eds. (Plenum, N.Y., in press).
Ward, H. E., et al., *Pharmacol. Biochem. Behav.* 60, 209 (1998).
Widom, C. S., *Science* 244, 160 (1989).
Widom, C. S., in *Handbook of Antisocial Behavior*, D. M. Stoff, J. Breiling, J. D. Maser, Eds. (Wiley, New York, 1997).
World Health Organization, *Comparative Quantification of Health Risks: Global and Regional Burden of Disease Due to Selected Risk Factors* (WHO, Geneva, in press).

```
SEQUENCE LISTING

<160> NUMBER OF SEQ ID NOS: 2

<210> SEQ ID NO 1
<211> LENGTH: 20
<212> TYPE: DNA
<213> ORGANISM: Homo sapiens

<400> SEQUENCE: 1
acagcctgac cgtggagaag                                                       20

<210> SEQ ID NO 2
<211> LENGTH: 20
<212> TYPE: DNA
<213> ORGANISM: Homo sapiens

<400> SEQUENCE: 2
gaacggacgc tccattcgga                                                       20
```

Morrell, V., *Science* 260, 1722 (1993).
Muthen, L. K., B. O. Muthen, *M-plus*. (Author, Los Angeles, 1999).
Parsian, A., C. R. Cloninger, *Psychiatric Genet.* 11, 89 (2001).
Pine, D., et al., *Arch. Gen. Psychiatry.* 54, 839 (1997).
Pollak, S. D., D. Cicchetti, R. Klorman, J. T. Brumaghim, *Child Develop.* 68, 773 (1997).
Poulton, R., et al., *Lancet*, in press (2002).
Raine, A., P. Brennan, S. A. Mednick, *Arch. Gen. Psychiatry* 51, 984 (1994).
Robins, L. N., *Psychol. Med.* 8, 611 (1978).
Rowe, D. C., *Biology and Crime* (Roxbury, Los Angeles, 2001).
Rutter, M. H. Giller, A. Hagell, *Antisocial Behavior by Young People* (Cambridge University Press, 1998).
Rutter, M., J. Silberg, *Annu. Rev. Psychology* 53, 463 (2002).
Sabol, S. Z., S. Hu, D. *Hamer, Hum. Genet.* 103, 273 (1998).
Samochowiec, J., et al., *Psychiatry Res.* 86, 72 (1999).
Satten, G. A., D. Flanders, Q. Yang, *Am. J. Hum. Genet.* 68 466 (2001).

We claim:

1. A method for assessing predisposition to a mental disorder phenotype selected from the group consisting of a conduct disorder, violent behavior and antisocial behavior in a human subject who has experienced childhood maltreatment, the method comprising the steps of:
   determining whether the subject carries a two- or three-repeat allele of a variable number tandem repeat polymorphism within a gene encoding human monoamine oxidase A enzyme, wherein a locus of the gene is amplified by SEQ ID NO:1 and SEQ ID NO:2; and
   concluding that the subject is predisposed to the phenotype if the subject carries the two- or three-repeat allele.

2. The method of claim 1 wherein the subject carries the two or three repeat allele.

3. The method of claim 1 further comprising the step of counseling the subject to pursue or avoid a particular type of employment.

4. The method of claim 1 further comprising the step of counseling the subject to avoid the childhood maltreatment.

5. The method of claim 1 further comprising the step of prescribing a therapy selected from the group consisting of psychological therapy and pharmaceutical therapy.

* * * * *